US009320841B2

(12) United States Patent  
Bian et al.

(10) Patent No.: US 9,320,841 B2
(45) Date of Patent: Apr. 26, 2016

(54) VENTRICULAR ASSIST DEVICE (71) Applicant: Corvivo Inc., Coquitlam (CA)

(72) Inventors: Xiaoming Bian, Dalian (CN); Frank Zheng, Kirkland, WA (US)

(73) Assignee: Corvivo, Inc., Coquitlam, British Columbia (CA)

( * ) Notice: Subject to any disclaimer, the term of this patent is extended or adjusted under 35 U.S.C. 154(b) by 0 days.

(21) Appl. No.: 13/924,472

(22) Filed: Jun. 21, 2013

(65) Prior Publication Data

US 2014/0378744 A1 Dec. 25, 2014

(51) Int. Cl.
*A61M 1/12* (2006.01)
*A61M 1/10* (2006.01)

(52) U.S. Cl.
CPC ........... *A61M 1/1087* (2014.02); *A61M 1/1055* (2014.02); *A61M 1/1067* (2013.01); *A61M 1/1086* (2013.01); *A61M 1/1098* (2014.02); *A61M 1/125* (2014.02); *A61M 1/122* (2014.02); *A61M 2230/005* (2013.01); *A61M 2230/04* (2013.01)

(58) Field of Classification Search
CPC ........... A61M 1/1037; A61M 1/1043; A61M 1/1046; A61M 1/1055; A61M 1/1086
USPC ...................................... 600/16–18; 623/3.11
See application file for complete search history.

(56) References Cited

U.S. PATENT DOCUMENTS

| 3,768,931 | A | | 10/1973 | Willis, Jr. | |
|---|---|---|---|---|---|
| 4,185,617 | A | * | 1/1980 | Hutchins | 600/16 |
| 4,621,617 | A | | 11/1986 | Sharma | |
| 5,332,403 | A | | 7/1994 | Kolff | |
| 6,123,724 | A | | 9/2000 | Denker | |
| 6,251,061 | B1 | * | 6/2001 | Hastings et al. | 600/16 |
| 6,264,601 | B1 | * | 7/2001 | Jassawalla et al. | 600/16 |
| 7,273,446 | B2 | * | 9/2007 | Spence | 600/16 |
| 7,357,771 | B2 | * | 4/2008 | Peters et al. | 600/18 |
| 7,402,134 | B2 | | 7/2008 | Moaddeb et al. | |
| 8,303,481 | B2 | * | 11/2012 | Kassab et al. | 600/16 |
| 8,382,651 | B2 | * | 2/2013 | Kassab et al. | 600/16 |
| 2002/0151761 | A1 | * | 10/2002 | Viole et al. | 600/16 |
| 2004/0116769 | A1 | * | 6/2004 | Jassawalla et al. | 600/16 |
| 2009/0099498 | A1 | * | 4/2009 | Demers et al. | 604/6.09 |
| 2009/0292160 | A1 | | 11/2009 | Nieman | |

FOREIGN PATENT DOCUMENTS

| EP | 1486217 B1 | 5/2010 |
|---|---|---|
| EP | 2371405 A1 | 10/2011 |
| WO | WO96/04945 A1 | 2/1996 |
| WO | WO02/854677 A1 | 10/2002 |
| WO | WO2004/045677 A1 | 6/2004 |
| WO | WO2007/044601 A2 | 4/2007 |
| WO | WO2007/087014 A3 | 8/2007 |
| WO | WO2014/201575 A1 | 12/2014 |

OTHER PUBLICATIONS

WIPO, Canadian International Search Authority, International Search Report and Written Opinion mailed Nov. 24, 2014 in International Patent Application No. PCT/CA2014/050598, 9 pages.

* cited by examiner

*Primary Examiner* — Allen Porter, Jr.
(74) *Attorney, Agent, or Firm* — Inskeep IP Group, Inc.

(57) ABSTRACT

A ventricle assist device comprises an inlet for receiving blood, an outlet for discharging blood, and a chamber disposed between the inlet and the outlet. There is also a means for actuating the ventricle assist device between an expanded configuration and a contracted configuration. In the expanded configuration blood flows into the inlet. In the contracted configuration blood flows out of the outlet. There may be a one-way valve at the outlet for preventing blood flow back into the chamber. The one-way valve is a diaphragm valve. The chamber may have a resilient outer wall. The chamber may have an ovoid shape.

8 Claims, 7 Drawing Sheets

VENTRICULAR ASSIST DEVICE

BACKGROUND OF THE INVENTION

1. Field of the Invention

The present invention relates to ventricular assist devices and, in particular, to implantable ventricular assist devices.

2. Description of the Related Art

It is known to use intra-aortic balloon heart pumps, operating in counterpulsation, to assist heart function. There are however a number of known risks associated with intra-aortic balloon heart pumps including thromboembolism, vessel injury and tissue ischemia. Intra-aortic balloon pumps may also be insufficient to sustain hemodynamics if the left heart is severely injured. There have accordingly been a number of alternative devices developed for assisting heart function in patients with chronic heart failure. For example, U.S. Pat. No. 7,357,771 which issued on Apr. 15, 2008 to Peters et al., and the full disclosure of which is incorporated herein by reference, discloses a device for use in assisting patient heart function. The device comprises an aortic compression means which may be fully implantable, a fluid reservoir, and a pump means adapted to pump a fluid from the reservoir to the aortic compression means so as to actuate the aortic compression means at least partly in counterpulsation with the patient's heart. In addition, the device is adapted to be wholly positioned within the right chest cavity of the patient. The aortic compression means of the device may be curved along its length so as to substantially replicate the curve of the ascending aorta. The device may be easily implanted and there is a low risk of complications However, devices that repeatedly compress the aorta may damage the aorta and there is accordingly an ongoing need for improved ventricular assist devices.

SUMMARY OF THE INVENTION

There is provided a ventricle assist device comprising an inlet for receiving blood, an outlet for discharging blood, and a chamber disposed between the inlet and the outlet. There is also a means for actuating the ventricle assist device between an expanded configuration and a contracted configuration. In the expanded configuration blood flows into the inlet. In the contracted configuration blood flows out of the outlet. There may be a one-way valve at the outlet for preventing blood flow back into the chamber. The one-way valve is a diaphragm valve. The chamber may have a resilient outer wall. The chamber may have an ovoid shape.

The means for actuating the ventricle assist between the expanded configuration and the contracted configuration may include a first pad disposed on the resilient outer wall of the chamber and a second pad disposed on the outer wall of the chamber opposite of the first pad. The first pad may have a magnetic field generator and the second pad may have a material which is attracted to the magnetic field generator when the magnetic field generator generates a magnetic field. The second pad may move towards the first pad when the magnetic field generator generates a magnetic field, and thereby actuate the ventricle assist device to the contracted configuration by contracting the resilient outer wall of the chamber. The resilient outer wall of the chamber may actuate the ventricle assist device to the expanded configuration when the magnetic field generator is not generating a magnetic field and the material is not attracted to the magnetic field generator.

The means for actuating the ventricle assist between the expanded configuration and the contracted configuration may alternatively include a magnetic field generator integral with the resilient outer wall of the chamber and a material integral with the resilient outer wall of the chamber which is attracted to the magnetic field generator when the magnetic field generator generates a magnetic field. The material may move toward the magnetic field generator when the magnetic field generator generates a magnetic field and thereby actuate the ventricle assist device to the contracted configuration by contracting the resilient outer wall of the chamber. The resilient outer wall of the chamber may actuate the ventricle assist device to the expanded configuration when the magnetic field generator is not generating a magnetic field and the material is not attracted to the magnetic field generator.

The ventricle assist device may further include an electrical energy supply electrically connected to the magnetic field generator, a controller which drives the electric energy supply to either energize or de-energize the magnetic field generator, and an ECG signal generator which signals the controller when there is ventricular diastole and ventricular systole. The controller may drive the electrical energy supply to energize the magnetic field generator when the ECG signal generator signals the controller that there is ventricular diastole. The controller may drive the electrical energy supply to de-energize the magnetic field generator when the ECG signal generator signals the controller that there is ventricular systole.

There is also provided a method of left ventricle assist comprising removing a portion of the aorta distal of the native aortic valve and implanting a ventricle assist device to replace the removed portion of the aorta. The ventricle assist device comprising an inlet for receiving blood, an outlet for discharging blood, and a chamber disposed between the inlet and the outlet. There is also a means for actuating the ventricle assist device between an expanded configuration and a contracted configuration. In the expanded configuration blood flows into the inlet. In the contracted configuration blood flows out of the outlet. The ventricle assist device is actuated to the expanded configuration during ventricle systole and the ventricle assist device is actuated to the contracted configuration during ventricle diastole.

There is further provided a method of right ventricle assist comprising removing a portion of the pulmonary artery distal of the native pulmonic valve and implanting a ventricle assist device to replace the removed portion of the pulmonary artery. The ventricle assist device comprising an inlet for receiving blood, an outlet for discharging blood, and a chamber disposed between the inlet and the outlet. There is also a means for actuating the ventricle assist device between an expanded configuration and a contracted configuration. In the expanded configuration blood flows into the inlet. In the contracted configuration blood flows out of the outlet. The ventricle assist device is actuated to the expanded configuration during ventricle systole and the ventricle assist device is actuated to the contracted configuration during ventricle diastole.

BRIEF DESCRIPTIONS OF DRAWINGS

The invention will be more readily understood from the following description of the embodiments thereof given, by way of example only, with reference to the accompanying drawings, in which.

DESCRIPTIONS OF THE PREFERRED EMBODIMENTS

Figure 1:
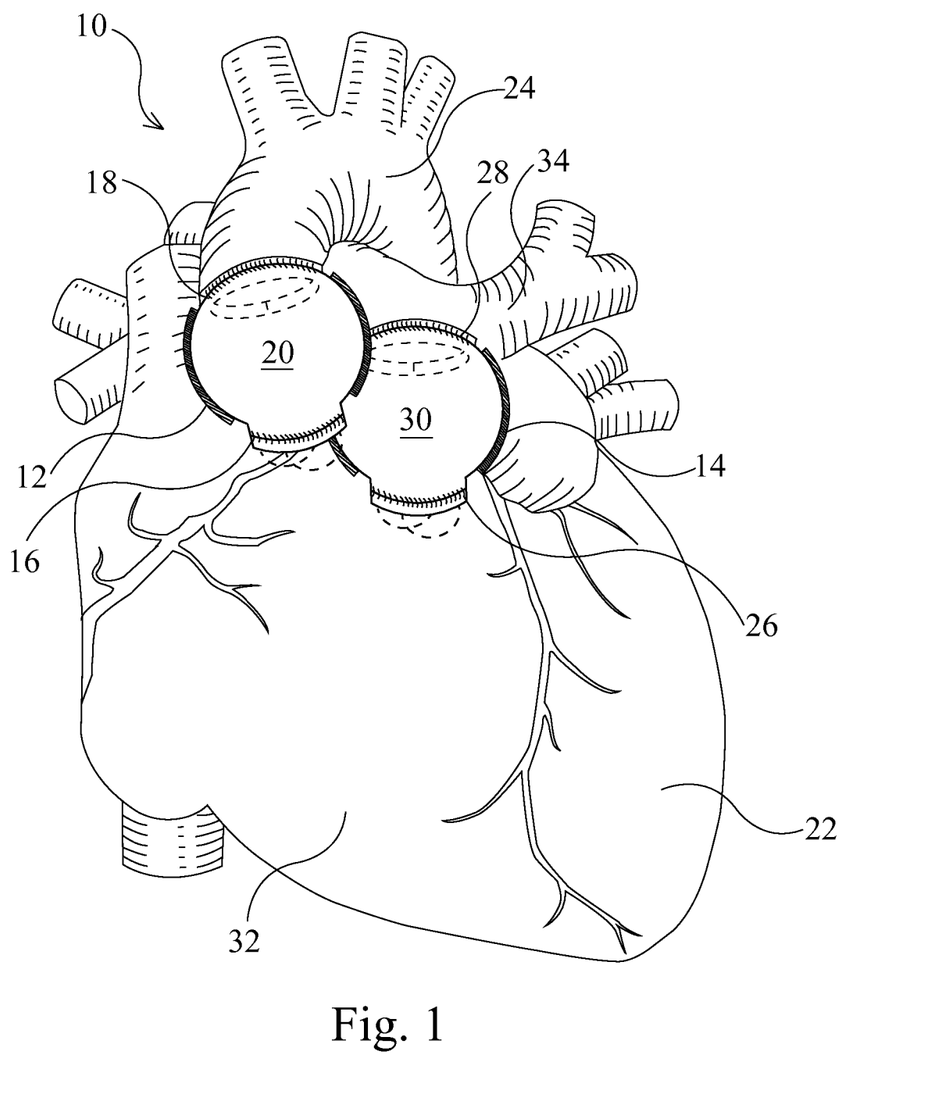
FIG. 1 is a fragmentary, sectional view of a biventricular failed heart provided with an implanted left ventricle assist device and an implanted right ventricle assist device.

Referring to the drawings and first to FIG. 1, there is shown a biventricular failed heart 10 provided with an implanted left ventricle assist device 12 and an implanted right ventricle assist device 14. The left ventricle assist device 12 generally comprises an inlet 16, an outlet 18, and a chamber 20 disposed between the inlet 16 and the outlet 18. The inlet 16 of the left ventricle assist device 12 is in fluid communication with a failed left ventricle 22 of the heart 10 and the outlet 18 of the left ventricle assist device is surgically connected to and in fluid communication with the aorta 24. The left ventricle assist device 12 accordingly assists blood flow from the left ventricle 22 to the aorta 24. More specifically, a portion of the aorta 24 distal of the native aortic valve (not shown) is removed and replaced by the left ventricle assist device 12. The inlet 16 of the left ventricle assist device 12 is connected to a proximal open end of the aorta 24. The outlet 18 of the left ventricle assist device 12 is connected to a distal open end of the aorta 24. The failed left ventricle 22 functions as a pathway for blood flow from the left atrium to the aorta 24 as well as a blood reservoir as will be described below.

Likewise the right ventricle assist device 14 generally comprises an inlet 26, an outlet 28, and a chamber 30 disposed between the inlet 26 and the outlet 28. The inlet 26 of the right ventricle assist device 14 is in fluid communication with the right ventricle 32 of the heart 10 and the outlet 28 of the left ventricle assist device is surgically connected to and in fluid communication with the pulmonary artery 34. The right ventricle assist device 14 accordingly allows for blood flow from the right ventricle 32 to the pulmonary artery 34. More specifically, a portion of the pulmonary artery 34 distal of the native pulmonic valve (not shown) is removed and replaced by the right ventricle assist device 14. The inlet 26 of the right ventricle assist device 14 is surgically connected to a proximal open end of the pulmonary artery 34. The outlet 28 of the right ventricle assist device 14 is connected to a distal open end of the pulmonary artery 34. The failed right ventricle 32 functions as a pathway for blood flow from right atrium to the pulmonary artery 34 as well as a blood reservoir as will be described below.

The left ventricle assist device 12 and the right ventricle assist device 14 have a substantially identical structure and function in a substantially identical manner. Accordingly, only the left ventricle assist device 12 is described in detail herein with the understanding that the right ventricle assist device 14 has a substantially identical structure and functions in a substantially identical manner. The left ventricle assist device 12 is shown in greater detail in FIG. 2 and is provided with a one-way valve 36 at the outlet 18 thereof. The one-way valve 36 is a diaphragm check valve in this example but any suitable one-way valve may be used. There is a resilient outer wall 38 which defines the chamber 20 of the left ventricle assist device 12. The resilient outer wall 38 and therefore the left ventricle assist device 12 are substantially ovoid in this example as this shape may prevent thrombosis formation. However, in other examples, the left ventricle assist device 12 may have any suitable geometry.

Figure 2:
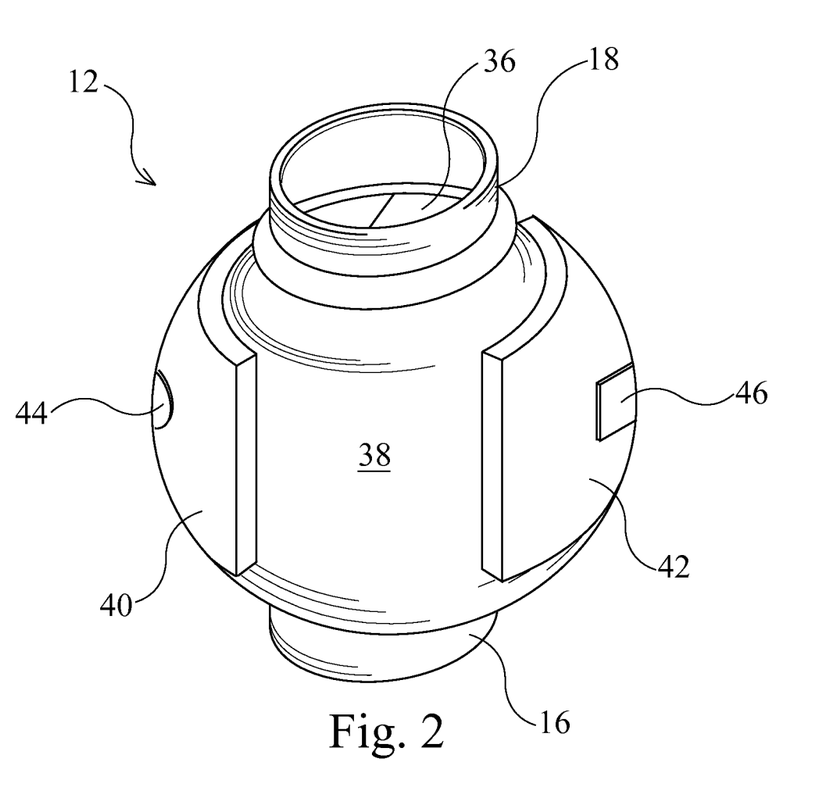
FIG. 2 is a perspective view of the left ventricle assist device of FIG. 1.

There are flexible pads 40 and 42 on opposite sides of the resilient outer wall 38. In this example, the pads 40 and 42 are symmetrical in shape but one of the pads 40 is provided with a magnetic field generator in the form of an electromagnet 44 while the other one the pads 42 is provided with a material 46 which will be attracted to the electromagnet 44 when the electromagnet 44 generates a magnetic field. The material 46 is a metal in this example. However, in other examples the material may be a magnetic field generator that generates a magnetic field having a polarity opposite to the magnetic field generated by the electromagnet 44. The electromagnet 44 and the material 46 may be disposed on or within their respective flexible pads 40 and 42. Alternatively, a magnetic field generator and a material which will be attracted to the magnetic field generator when the magnetic field generator generates a magnetic field may both be integral with the walls of outer wall of the chamber.

Figure 3:
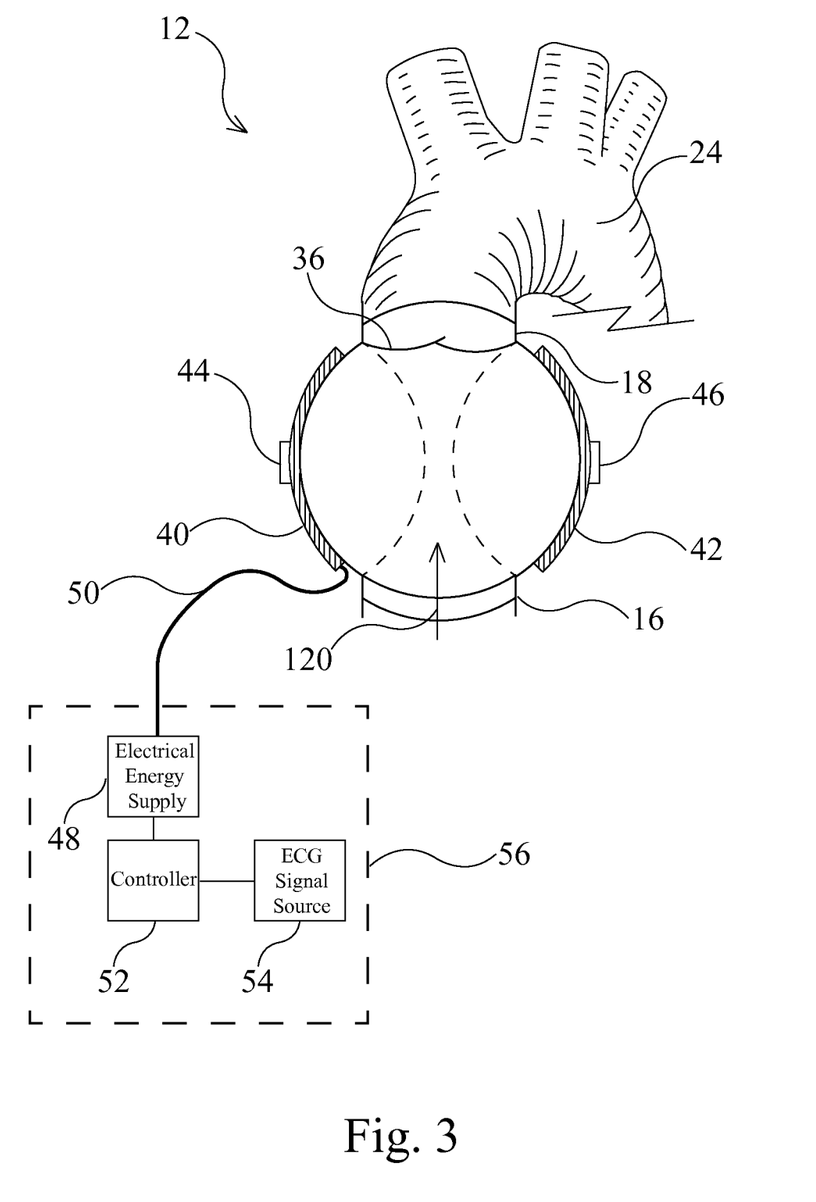
FIG. 3 is a sectional view of the left ventricle assist device of FIG. 1 in an expanded configuration.
Figure 4:
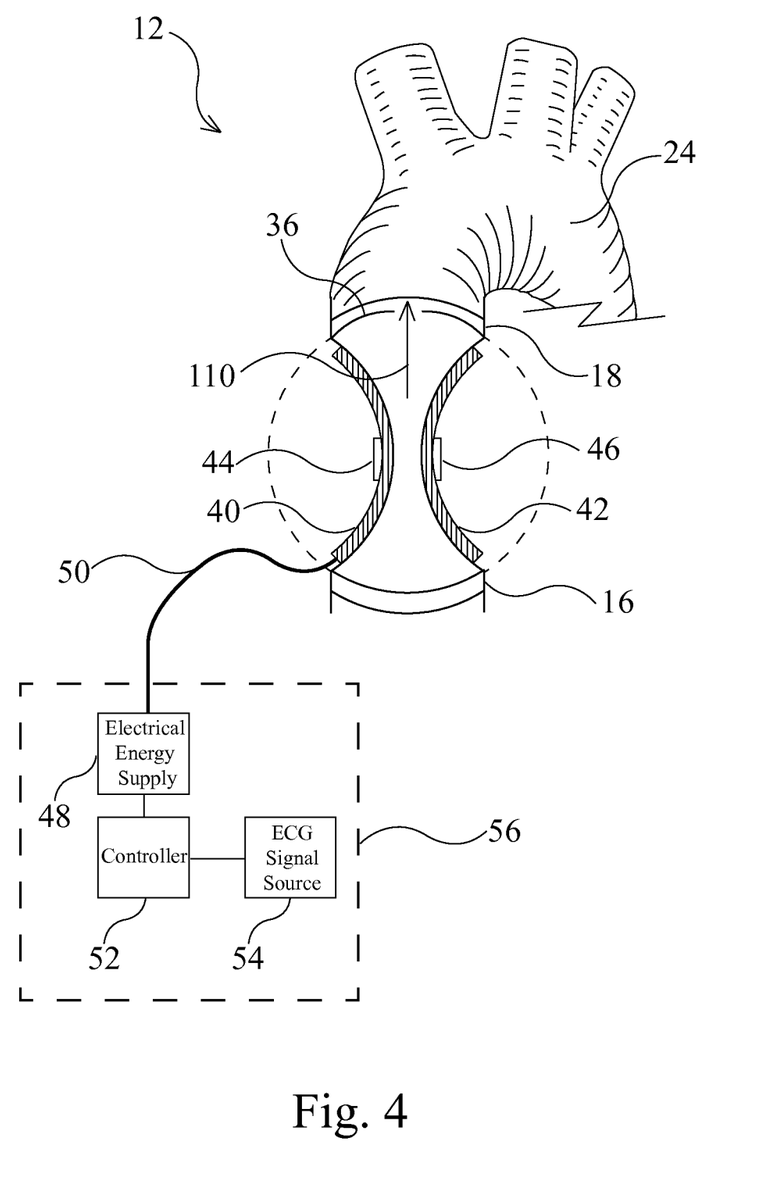
FIG. 4 is a sectional view of the left ventricle assist device of FIG. 1 in a contracted configuration.
Figure 5:
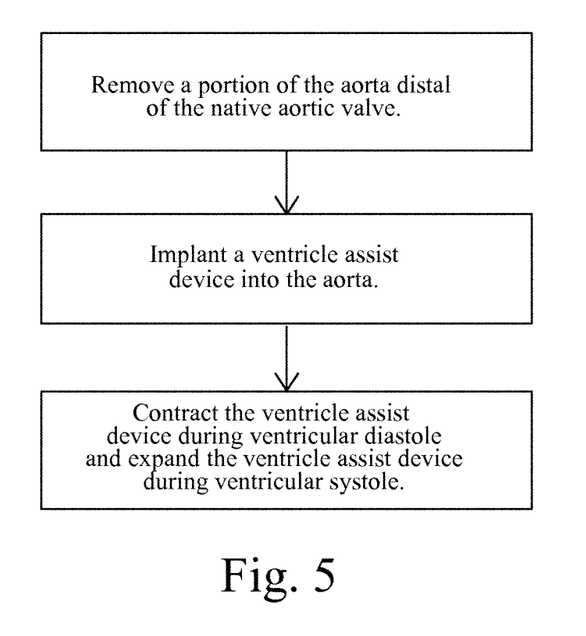
FIG. 5 is flowchart showing a method for providing left ventricle assist.
Figure 6:
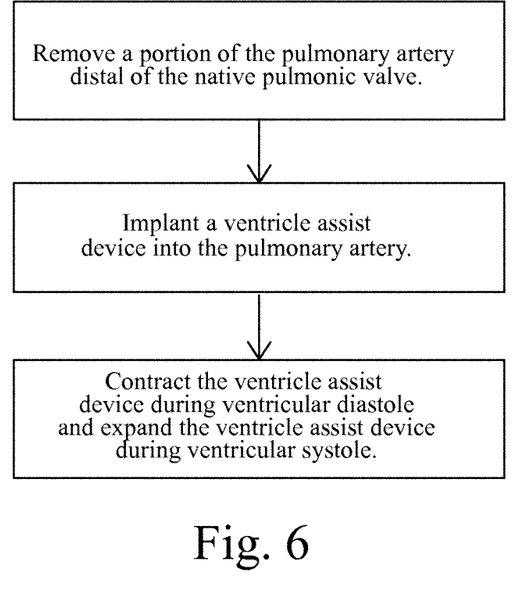
FIG. 6 is a flowchart showing a method for providing right ventricle assist.
Figure 7:
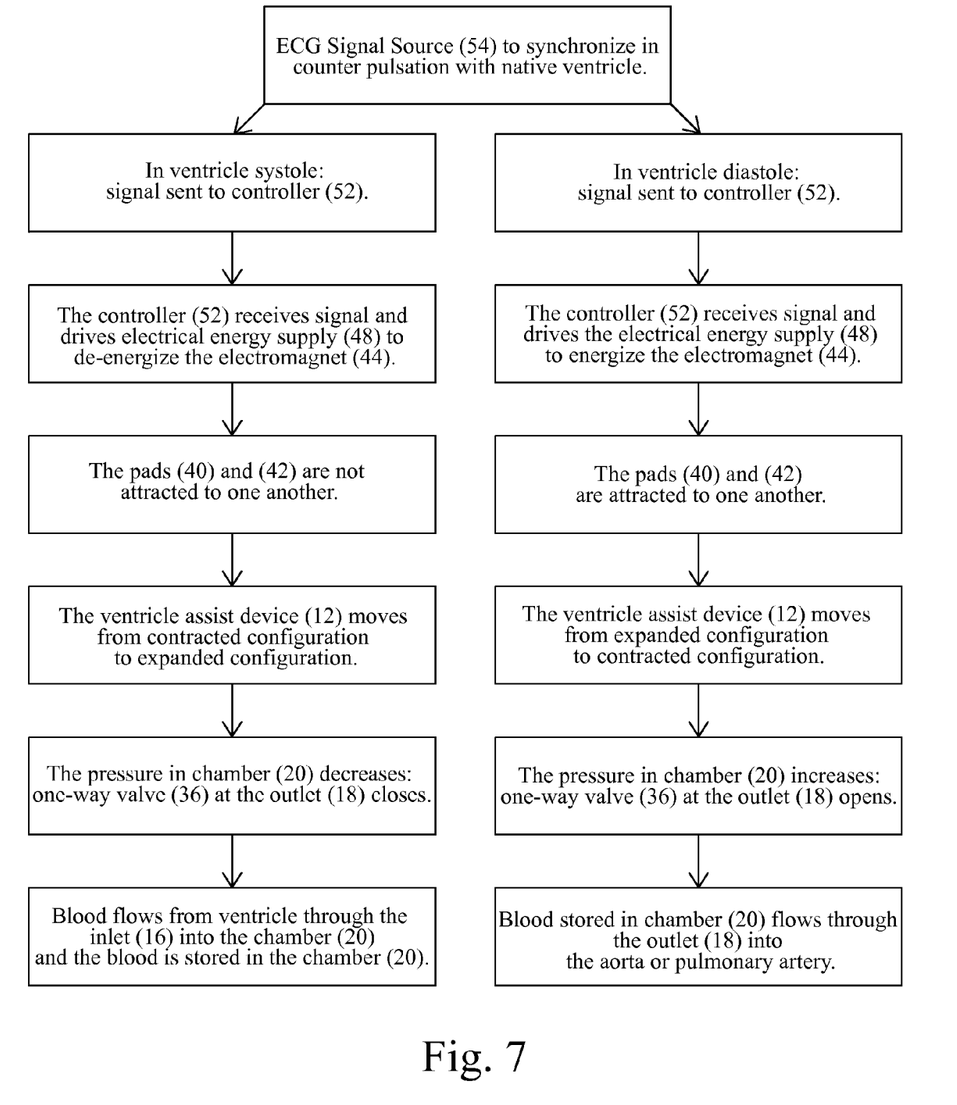
FIG. 7 is a flowchart showing operation of the ventricle assist devices of FIG. 1.

Referring now to FIGS. 3 and 4, operation of the left ventricle assist device 12 is shown. In FIG. 3 the left ventricle assist device 12 is shown in an expanded configuration. In FIG. 4 the left ventricle assist device 12 is shown in a contracted configuration. An electrical energy supply 48, for example a battery, is in electrically connected with the electromagnet 44 via an electrical conductor which, in this example, is a wire 50. The electrical energy supply 48 is driven by a controller 52 which receives signals from an ECG signal source 54. The controller 52 drives the electrical energy supply 48 to energize the electromagnet 44 when the ECG signal source 54 signals that there is ventricular diastole and the controller 52 drives the electrical energy supply 48 to de-energize the electromagnetic 44 when the ECG signal source 54 signals that there is ventricular systole. The electrical energy supply 48, the controller 52, and the ECG signal source 54 may all be part of an implanted pacemaker type device 56.

The left ventricle assist device 12 moves from the expanded configuration to the contracted configuration when the electromagnetic 44 is energized. This is because electromagnet 44 and the material 46 in the respective flexible pads 40 and 42 are then drawn towards one another. The pressure differential when the left ventricle assist device 12 is in the contracted configuration opens the one-way valve 36 and blood in the chamber 20 flows into the aorta 24 through the outlet 18 as indicated generally by arrow 110 in FIG. 4. The left ventricle assist device 12 moves from the contracted configuration to the expanded configuration when the electromagnetic 44 is de-energized. This is because the electromagnetic 44 and the material 46 in the respective flexible pads 40 and 42 are no longer attracted to one another and the resilient nature of the resilient outer wall 38 actuates the left ventricle assist device 12 to move to the expanded configuration. The pressure differential when the left ventricle assist device 12 is in the expanded configuration closes the one-way valve 36. Accordingly, blood which flows into the chamber 20 through the inlet 16, as shown generally by arrow 120 in FIG. 3, is stored in the chamber and the chamber temporarily functions as a blood reservoir.

In operation, a portion of the ascending aorta is surgically removed and the left ventricle assist device 12 is implanted to replace the removed portion of the aorta. The two pads 40 and 42 are disposed on the resilient outer wall 38 of the chamber 20 on opposite sides of the resilient outer wall 38. One of the pads 40 is provided with the electromagnet 44 the other one of the pads 42 is provided with the material 46 which is attracted to the electromagnet 44 when the electromagnet 44 generates a magnetic field. The electromagnet 44 is connected to the implanted pacemaker type device 56 through the wire 50. The implanted pacemaker type device 56 senses the patient's ECG and energizes and de-energizes the electromagnet 44 based on the patient's ECG. The electromagnet 44 is de-energized and the ventricle assist device 12 moves from the contracted configuration to the expanded configuration when the failed left ventricle 22 contracts as indicated by an R wave of the ECG. The one-way valve 36 at the outlet 18 simultaneously closes and the pressure inside chamber 20 decreases while the native left ventricle valve opens. The result is blood flow from the failed left ventricle 22 through the inlet 16 and into the chamber 20 of the left ventricle assist device 12. The electromagnet is then energized and the ventricle assist device 12 moves from the expanded configuration to the contracted configuration when the failed left ventricle 22 relaxes as indicated by a T wave of the ECG. The one-way valve 36 at outlet 18 simultaneously opens so the blood stored in the chamber 20 flows into the aorta 24. The left ventricle may accordingly function merely as a pathway for blood flowing from left atrium to the left ventricle assist device 12 while the left ventricle assist device 12 functions as a pump.

The right ventricle assist device functions in a substantially similar manner with the exception that a portion of the pulmonary trunk is surgically removed and the right ventricle assist device 14 is implanted to replace the removed portion of the pulmonary trunk. The right ventricle may then merely function as a pathway for blood flowing from the right atrium to the right ventricle assist device 14 while the right ventricle assist device 14 functions as a pump.

The ventricle assist device disclosed herein may be fully implanted and replace the function of a late stage or fully failed ventricle. Blood volume per stroke may be designed into the shape and contraction means to normal ventricle performance levels. Blood volume per stroke may be independent of ventricle performance. The ventricle assist device may be provided with one-way or back-flow prevention valve to improve efficiency.

It will be understood by person skilled in the art that although in this example the means for actuating the ventricle assist device between the expanded configuration and the contracted configuration is an electromagnetic means that in other examples other means, for example, mechanical means, hydraulic means, electrical means, etc. may be used to actuate the ventricle assist device between the expanded configuration and the contracted configuration.

It will also be understood by a person skilled in the art that many of the details provided above are by way of example only, and are not intended to limit the scope of the invention which is to be determined with reference to the following claims.

What is claimed is:

1. A ventricle assist device comprising:
   an inlet for receiving blood;
   an outlet for discharging blood;
   a chamber having a resilient outer wall disposed between the inlet and the outlet;
   a first pad disposed on the resilient outer wall of the chamber, the first pad having a magnetic field generator;
   a second pad disposed on the resilient outer wall of the chamber opposite of the first pad, the second pad having a material which is attracted to the magnetic field generator when the magnetic field generator generates a magnetic field, wherein the second pad moves towards the first pad when the magnetic field generator generates a magnetic field and thereby actuates the ventricle assist device to a contracted configuration by contracting the resilient outer wall of the chamber, and wherein the resilient outer wall of the chamber actuates the ventricle assist device to an expanded configuration when the magnetic field generator is not generating a magnetic field and the material is not attracted to the magnetic field generator;
   an electrical energy supply electrically connected to the magnetic field generator;
   a controller which drives the electric energy supply to either energize or de-energize the magnetic field generator; and
   an ECG signal generator which signals the controller when there is ventricular diastole and ventricular systole, wherein the controller drives the electrical energy supply to energize the magnetic field generator when the ECG signal generator signals the controller that there is ventricular diastole and wherein the controller drives the electrical energy supply to de-energize the magnetic field generator when the ECG signal generator signals the controller that there is ventricular systole.

2. The ventricle assist device as claimed in claim 1 further including a one-way valve at the outlet for preventing blood flow back into the chamber.

3. The ventricle assist device as claimed in claim 2 wherein the one-way valve is a diaphragm valve.

4. The ventricle assist device as claimed in claim 1 wherein chamber has an ovoid shape.

5. A ventricle assist device comprising:
   an inlet for receiving blood;
   an outlet for discharging blood;
   a chamber having a resilient outer wall disposed between the inlet and the outlet;
   a magnetic field generator in the resilient outer wall of the chamber;
   a material in the resilient outer wall of the chamber which is attracted to the magnetic field generator when the magnetic field generator generates a magnetic field, wherein the material moves towards the magnetic field generator when the magnetic field generator generates a magnetic field and thereby actuates the ventricle assist device to the contracted configuration by contracting the resilient outer wall of the chamber, and wherein the resilient outer wall of the chamber actuates the ventricle assist device to the expanded configuration when the magnetic field generator is not generating a magnetic field and the material is not attracted to the magnetic field generator;
   an electrical energy supply electrically connected to the magnetic field generator;
   a controller which drives the electric energy supply to either energize or de-energize the magnetic field generator; and
   an ECG signal generator which signals the controller when there is ventricular diastole and ventricular systole, wherein the controller drives the electrical energy supply to energize the magnetic field generator when the ECG signal generator signals the controller that there is ventricular diastole and wherein the controller drives the electrical energy supply to de-energize the magnetic field generator when the ECG signal generator signals the controller that there is ventricular systole.

6. The ventricle assist device as claimed in claim 5 further including a one-way valve at the outlet for preventing blood flow back into the chamber.

7. The ventricle assist device as claimed in claim 6 wherein the one-way valve is a diaphragm valve.

8. The ventricle assist device as claimed in claim 5 wherein chamber has an ovoid shape.

* * * * *